(12) United States Patent
Waldman et al.

(10) Patent No.: US 9,308,330 B2
(45) Date of Patent: Apr. 12, 2016

(54) MOTORIZED DRUG DELIVERY DEVICE WITH NEEDLES AND ROLLER

(71) Applicants: Amir Waldman, Yarqona (IL); Tal Presenty, Tel-Mond (IL)

(72) Inventors: Amir Waldman, Yarqona (IL); Tal Presenty, Tel-Mond (IL)

(73) Assignee: Roller Jet Ltd., Moshav Yarkona (IL)

( * ) Notice: Subject to any disclaimer, the term of this patent is extended or adjusted under 35 U.S.C. 154(b) by 348 days.

(21) Appl. No.: 13/938,243

(22) Filed: Jul. 10, 2013

(65) Prior Publication Data

US 2015/0018797 A1    Jan. 15, 2015

(51) Int. Cl.
| | |
|---|---|
| *A61M 5/00* | (2006.01) |
| *A61M 31/00* | (2006.01) |
| *A61M 5/315* | (2006.01) |
| *A61M 5/32* | (2006.01) |
| *A61M 5/20* | (2006.01) |
| *A61M 5/31* | (2006.01) |
| *A61M 37/00* | (2006.01) |

(52) U.S. Cl.
CPC .............. *A61M 5/31511* (2013.01); *A61M 5/20* (2013.01); *A61M 5/3137* (2013.01); *A61M 5/31583* (2013.01); *A61M 5/3295* (2013.01); *A61M 5/31575* (2013.01); *A61M 2037/0023* (2013.01); *A61M 2205/8206* (2013.01)

(58) Field of Classification Search
CPC .......... A61M 5/31511; A61M 5/3295; A61M 2037/0023; A61M 2205/8206; A61M 5/20; A61M 5/3137; A61M 5/31575; A61M 5/31583
USPC .......................................................... 604/506
See application file for complete search history.

(56) References Cited

U.S. PATENT DOCUMENTS

| | | | | |
|---|---|---|---|---|
| 5,139,029 | A  * | 8/1992 | Fishman et al. .............. | 600/556 |
| 2009/0299328 | A1 * | 12/2009 | Mudd et al. .................... | 604/506 |
| 2012/0004638 | A1 * | 1/2012 | Zimmerman et al. ........ | 604/506 |

* cited by examiner

*Primary Examiner* — Jason Flick
(74) *Attorney, Agent, or Firm* — Dekel Patent Ltd.; David Klein

(57) ABSTRACT

A delivery device (10) includes a roller (12) rotatably mounted on an axle (14), a reservoir (40), and one or more hollow needles (16) positioned in the roller (12) in fluid communication with the reservoir (40). As the roller (12) rotates about the longitudinal axis (17) of the axle (14), a piston (30) pushes contents of the reservoir (40) through the needles (16). An actuator (36) is operatively connected to the piston (30) for increasing a pushing force of the piston (30).

9 Claims, 4 Drawing Sheets

MOTORIZED DRUG DELIVERY DEVICE WITH NEEDLES AND ROLLER

FIELD OF THE INVENTION

The present invention generally relates to drug delivery through the skin, such as for skin treatment and rejuvenation, but also for delivery of drugs such as insulin and others.

BACKGROUND OF THE INVENTION

U.S. Pat. No. 8,353,871 describes a drug delivery device that includes a roller with hollow needles and a drug reservoir for delivering the drug through the needles as the roller is passed over the skin. The roller is rotatably mounted on an axle. As the roller rotates about the axle, contents of the reservoir pass through the hollow needles. The roller and a piston slide with respect to other as the roller rotates about the axle. The relative sliding motion causes the piston to push contents of the reservoir through the needles.

SUMMARY OF THE INVENTION

The present invention seeks to provide improvements to the drug delivery device of U.S. Pat. No. 8,353,871, as is described more in detail hereinbelow. The terms drug, substance and medicament are used interchangeably throughout the description and claims.

There is thus provided in accordance with an embodiment of the present invention a delivery device including a roller rotatably mounted on an axle, a reservoir, at least one hollow needle positioned in the roller and in fluid communication with the reservoir, wherein as the roller rotates about a longitudinal axis of the axle, contents of the reservoir pass through the at least one hollow needle, and a piston arranged with respect to the roller such that there is relative sliding motion between the roller and the piston as the roller rotates about the longitudinal axis of the axle, the relative sliding motion causing the piston to push contents of the reservoir through the at least one needle, and an actuator operatively connected to the piston for increasing a pushing force of the piston that pushes the contents of the reservoir through the at least one needle.

In accordance with an embodiment of the present invention the actuator includes a motor coupled to the axle for rotating the axle, and the piston is threadedly coupled to the axle, such that increased torque supplied by the actuator to rotate the axle increases the pushing force of the piston.

In accordance with an embodiment of the present invention the actuator is coupled to the axle via a reduction gear.

In accordance with an embodiment of the present invention there is a plurality of needles, and a guard member overlies a portion of the needles. The guard member is arcuate and may subtend an angle greater than 180°.

In accordance with another embodiment of the present invention the actuator includes a linear actuator or solenoid arranged to push the piston. In another embodiment the actuator is pneumatic or hydraulic.

In accordance with an embodiment of the present invention piston is in threaded connection with the axle and the piston moves axially along the axle as the axle rotates about the longitudinal axis.

In accordance with an embodiment of the present invention a handle is provided for grasping by a user, the roller rotating with respect to the handle.

There is also provided in accordance with an embodiment of the present invention a method for puncturing skin including placing the device of the invention on the skin, and rotating the roller along the skin either manually or by means of the actuator, wherein as the roller rotates, the at least one hollow needle punctures the skin and contents of the reservoir pass through the at least one hollow needle into the skin.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Reference is now made to FIGS. 1-4, which illustrate a drug delivery device 10, constructed and operative in accordance with a non-limiting embodiment of the present invention.

Figure 1:
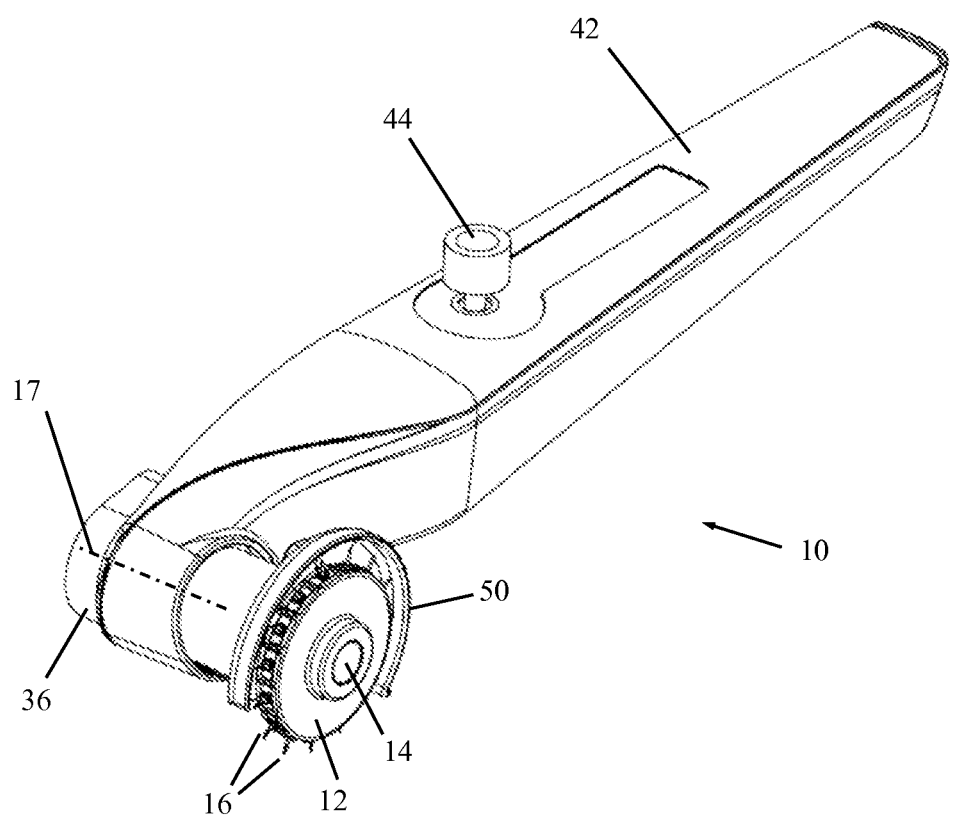
FIG. 1 is a simplified pictorial illustration of a drug delivery device, constructed and operative in accordance with an embodiment of the present invention.
Figure 2A:
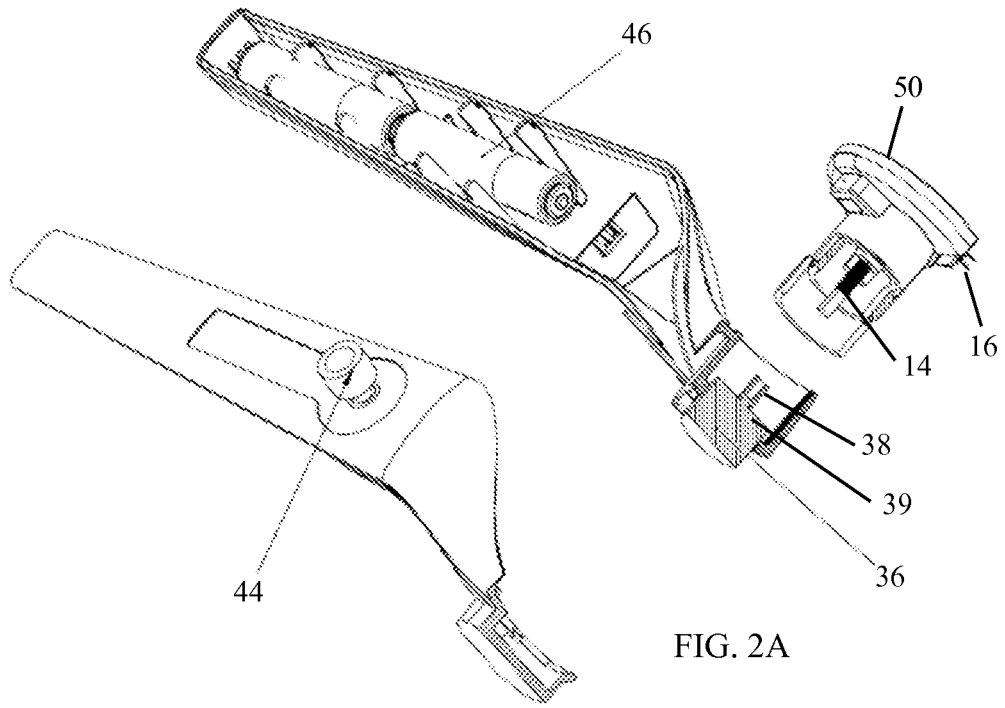
FIGS. 2A and 2B are simplified exploded illustrations of the drug delivery device of FIG. 1.
Figure 2B:
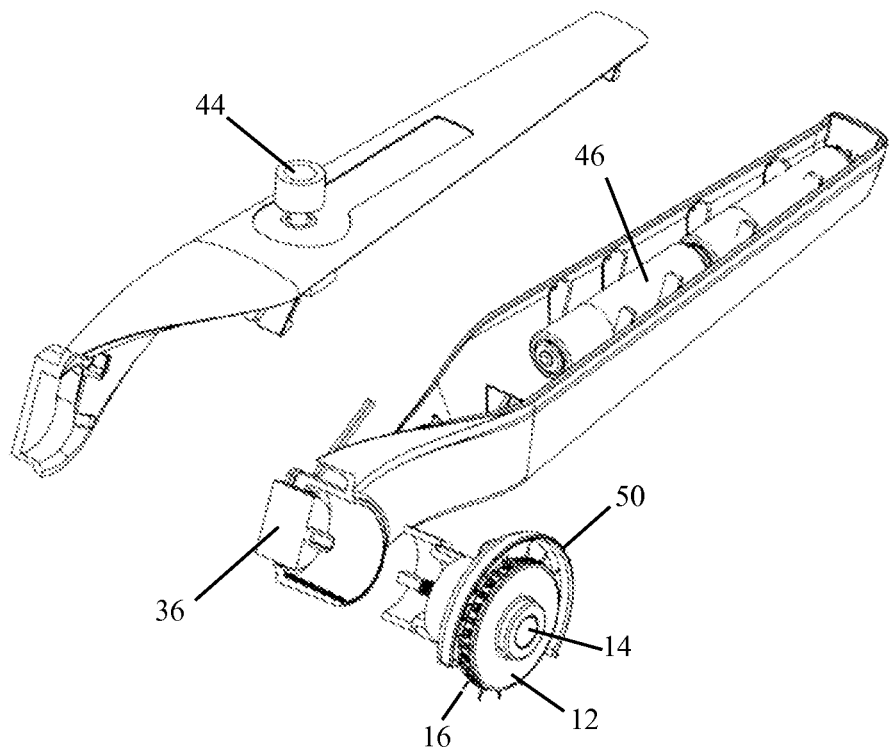
Figure 3:
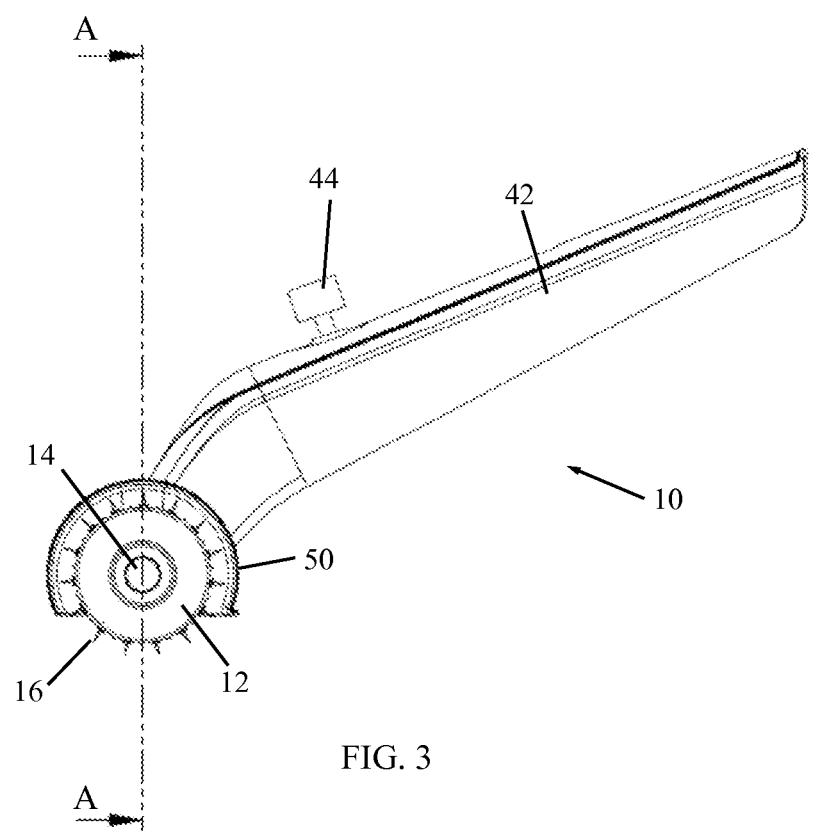
FIG. 3 is a simplified side-view illustration of the drug delivery device of FIG. 1.
Figure 4:
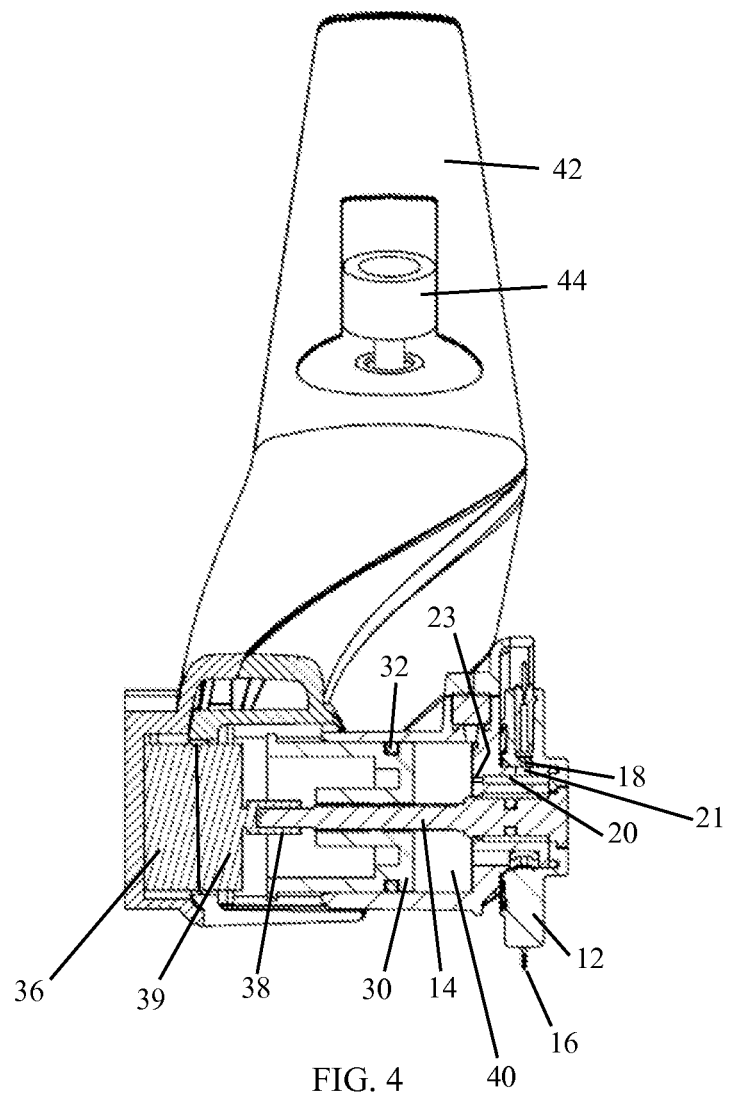
FIG. 4 is a simplified sectional illustration of the drug delivery device, taken along lines A-A in FIG. 3.

Device 10 includes a roller 12 rotatably mounted on an axle 14. One or more hollow needles 16 protrude radially outwards from the outer contour of the roller 12. In the illustrated embodiment, there is a plurality of needles 16 circumferentially spaced about a longitudinal axis 17 of axle 14. As seen in FIG. 4, a proximal end 18 of each needle 16 (i.e., the end opposite the tip of the needle) fluidly communicates with a channel 20 (such as via a passageway 21), which in turn is in fluid communication with a reservoir 40 (such as via a passageway 23).

A piston 30 is arranged for sliding motion with respect to roller 12. In the illustrated embodiment, axle 14 is threaded and piston 30 is in threaded engagement with axle 14, such that as axle 14 rotates, piston 30 advances linearly towards roller 12. Piston 30 slides in reservoir 40 and is sealed in its sliding movement by seals, such as O-rings 32. A substance to be delivered to a subject is stored in reservoir 40.

A handle 42 is provided for grasping by a user. Roller 12 rotates relative to axle 14 and to handle 42. To use the device 10 manually, the user grasps handle 42 and places device 10 on skin to be punctured. The user then rolls the device 10 along on the skin, causing roller 12 to rotate about axle 14. As roller 12 rotates about axle 14, simultaneously there is relative sliding motion between roller 12 and piston 30. Specifically, in the non-limiting illustrated embodiment, as roller 12 rotates about the longitudinal axis 17 of axle 14, piston 30 advances linearly towards roller 12 and pushes the contents of reservoir 40 through the needles 16 for delivery to the patient through the skin.

In accordance with an embodiment of the invention, an actuator 36 is operatively connected to piston 30 for increasing the pushing force of piston 30 that pushes the contents of reservoir 40 through needles 16. In one embodiment, actuator 36 is a DC motor coupled to axle 14 with a coupling 38 (FIG. 4) for rotating axle 14. The DC motor may include a reduction gear 39. The increased torque supplied by actuator 36 to rotate axle 14 increases the pushing force of piston 30. This may be especially helpful for substances with relatively high viscosity, which may be difficult to force through the needles 16 with manual power alone. A switch 44 may be provided on handle 42 for operating actuator 36. Batteries 46 may be disposed in handle 42 for powering actuator 36.

In accordance with an alternative embodiment of the invention, actuator 36 is a linear actuator or solenoid arranged to push piston 30. In such an embodiment, axle 14 is not threaded and piston 30 slides along axle 14 by the pushing force of actuator 36; there is no manual mode of operation, only operation by actuator 36. In another embodiment the actuator is pneumatic or hydraulic.

In accordance with an embodiment of the invention, a guard member 50 overlies a portion of needles 16. Guard member 50 may be arcuate and subtend an angle greater than 180°.

The device can be single-use (with disposable needles and roller, for example) or multiple-use, with the possibility of refilling the reservoir 40 (such as through refill holes, not shown).

What is claimed is:

1. A delivery device comprising:
    a roller rotatably mounted on an axle;
    a reservoir;
    at least one hollow needle positioned in said roller and in fluid communication with said reservoir, wherein as said roller rotates about a longitudinal axis of said axle, contents of said reservoir pass through said at least one hollow needle;
    a piston arranged with respect to said roller such that there is relative sliding motion between said roller and said piston as said roller rotates about the longitudinal axis of said axle, said relative sliding motion causing said piston to push contents of said reservoir through said at least one needle; and
    an actuator operatively connected to said piston for increasing a pushing force of said piston that pushes the contents of said reservoir through said at least one needle, and wherein said actuator comprises a motor coupled to said axle for rotating said axle, and said piston is threadedly coupled to said axle, such that increased torque supplied by said actuator to rotate said axle increases the pushing force of said piston.

2. The delivery device according to claim 1, wherein said actuator is coupled to said axle via a reduction gear.

3. The delivery device according to claim 1, wherein said at least one needle comprises a plurality of needles, and further comprising a guard member that overlies a portion of said needles.

4. The delivery device according to claim 3, wherein said guard member is arcuate.

5. The delivery device according to claim 3, wherein said guard member subtends an angle greater than 180°.

6. The delivery device according to claim 1, wherein said actuator comprises a linear actuator or solenoid arranged to push said piston.

7. The delivery device according to claim 1, wherein piston is in threaded connection with said axle and said piston moves axially along said axle as said axle rotates about said longitudinal axis.

8. The delivery device according to claim 1, further comprising a handle for grasping by a user, said roller rotating with respect to said handle.

9. A delivery device comprising:
    a roller rotatably mounted on an axle;
    a reservoir;
    at least one hollow needle positioned in said roller and in fluid communication with said reservoir, wherein as said roller rotates about a longitudinal axis of said axle, contents of said reservoir pass through said at least one hollow needle;
    a piston arranged with respect to said roller such that there is relative sliding motion between said roller and said piston as said roller rotates about the longitudinal axis of said axle, said relative sliding motion causing said piston to push contents of said reservoir through said at least one needle; and
    an actuator operatively connected to said piston for increasing a pushing force of said piston that pushes the contents of said reservoir through said at least one needle, and wherein piston is in threaded connection with said axle and said piston moves axially along said axle as said axle rotates about said longitudinal axis.

* * * * *